United States Patent
Berman

(10) Patent No.: US 9,248,159 B2
(45) Date of Patent: Feb. 2, 2016

(54) MRSA BACTERICIDAL TOPICAL GEL

(76) Inventor: Robert Stanley Berman, Jupiter, FL (US)

(*) Notice: Subject to any disclaimer, the term of this patent is extended or adjusted under 35 U.S.C. 154(b) by 706 days.

(21) Appl. No.: 13/299,093

(22) Filed: Nov. 17, 2011

(65) Prior Publication Data

US 2012/0128622 A1 May 24, 2012

Related U.S. Application Data

(63) Continuation-in-part of application No. 12/236,246, filed on Oct. 14, 2008, now abandoned.

(51) Int. Cl.
| | | |
|---|---|---|
| A61K 31/78 | (2006.01) | |
| A61P 31/04 | (2006.01) | |
| A61P 17/02 | (2006.01) | |
| A61K 38/14 | (2006.01) | |
| A61K 9/00 | (2006.01) | |
| A61K 47/10 | (2006.01) | |
| A61K 47/12 | (2006.01) | |
| A61K 47/18 | (2006.01) | |
| A61K 47/32 | (2006.01) | |
| A61K 47/36 | (2006.01) | |
| A61K 47/38 | (2006.01) | |
| A61L 26/00 | (2006.01) | |

(52) U.S. Cl.
CPC .............. *A61K 38/14* (2013.01); *A61K 9/0014* (2013.01); *A61K 47/10* (2013.01); *A61K 47/12* (2013.01); *A61K 47/18* (2013.01); *A61K 47/32* (2013.01); *A61K 47/36* (2013.01); *A61K 47/38* (2013.01); *A61L 26/008* (2013.01); *A61L 26/0066* (2013.01); *A61L 2300/406* (2013.01)

(58) Field of Classification Search
None
See application file for complete search history.

(56) References Cited

U.S. PATENT DOCUMENTS

| | | | |
|---|---|---|---|
| 5,670,169 A * | 9/1997 | Cornell et al. | ................ 424/488 |
| 5,905,092 A | 5/1999 | Osborne et al. | |
| 6,201,164 B1 | 3/2001 | Wulff et al. | |
| 6,331,309 B1 | 12/2001 | Jennings, Jr. et al. | |
| 6,914,051 B1 | 7/2005 | Allen | |
| 7,169,406 B2 | 1/2007 | Schultz | |
| 2009/0317467 A1 | 12/2009 | Moloney | |

OTHER PUBLICATIONS

Lin et al. Journal of Trauma: Injury, Infection and Critical Care (1999) 47(1): 136-141.*
Lin, S. et al, "In vitro elution of antiobtic from antibiotic-impregnated biodegradable calcium alginate wound dressing", Jrnl of Trauma: Injury, Infection and Critical Care, 47:1, (1999).

* cited by examiner

*Primary Examiner* — Marcela M Cordero Garcia
*Assistant Examiner* — Mindy Newman
(74) *Attorney, Agent, or Firm* — McHale & Slavin, P.A..

(57) ABSTRACT

The present invention is directed to an enhanced wound healing composition, including a gel containing vancomycin, useful for the prevention of the spread of resistant-type bacteria. Preferably, the drug is one or more antibiotic agents in therapeutically effective concentrations to reduce or eliminate MRSA. The composition is based on a gel composition containing one or more gel forming compounds, such as one or more polymers, preservatives, and/or pH stabilizers and buffers, which not only maintains a moist wound environment to enhance wound healing, but also provides an antibiotic agent which has sustained potency and stability. The composition, when placed in contact with a treatment site, delivers the drug to the site. By incorporating the drug into the gel composition that is formulated to enhance wound healing, the treatment of such disease is possible in a manner which promotes wound healing while reducing or eliminating the MRSA microbe.

28 Claims, 3 Drawing Sheets

MRSA BACTERICIDAL TOPICAL GEL

CROSS REFERENCE TO RELATED APPLICATIONS

This application is a continuation-in-part of and claims priority under 35 U.S.C. §120 to U.S. patent application Ser. No. 12/236,246, filed Oct. 14, 2008 now abandoned, entitled, "MRSA Bactericidal Topical Gel", the contents of which is herein incorporated by reference.

FIELD OF THE INVENTION

This invention relates to a bactericidal topical formulation for use in the prevention of the spread of bacterial infections; and more particularly to a unique vancomycin topical gel formulation and method of use for treatment of MRSA, characterized by sustained stability and potency.

BACKGROUND OF THE INVENTION

Use of antibiotics to treat disease is one of the most potent arsenals in modern medicine. These drugs are commonly prescribed to treat bacterial infections and work by killing the microbes, preventing them from reproducing, or allowing the natural defense systems of the body the ability to eliminate them. The continued use and overuse of certain antibiotics has lead to the development of antibiotic resistant bacteria strains. As particular antibiotics are used over time, bacterial strains have developed a survival strategy of mutation. The mutated bacteria are no longer killed by the antibiotics which results in longer and more serious infections. Once the bacteria become resistant to a particular antibiotic, a stronger antibiotic must be used to combat the disease. Stronger antibiotics may result in more serious side effects or harder treatment modalities, such as intravenous injecting verses oral pill forms, resulting in increased treatment costs.

*Staphylococcus aureus* is a common type of bacteria found in nearly 25% of healthy individuals. The bacteria usually live on the skin or in the nasal passages, but generally do not cause severe problems or infections. When a staph infection occurs, it is usually the result of the bacteria entering the body through a wound, such as a cut, sore, or through use of surgical equipment such as catheters or breathing tubes. Methicillin-resistant *Staphylococcus aureus*, or MRSA, is a particular strain of *Staphylococcus* bacteria that does not respond to many antibiotics. MRSA infection is spread by contact and has traditionally been found in hospitals, nursing centers, and other health care centers. Community Associated MRSA (CA-MRSA) infections (those infections found outside these traditional areas) has also been documented. Although many of these types of infections are restricted to certain populations in close quarters or contact, such as athletes, military, and prison inmates, MRSA infections within the general population are increasing.

Staph infections are treated with a class of antibiotics called beta-lectams, and include methicillin, oxacillin, penicillin, and amoxicillian. MRSA infections, however, have become resistant to many of these common antibiotics. Accordingly, treatment of MRSA infections includes using a variety of antibiotics in which the bacteria has not developed any resistance, such as vancomycin. Vancomycin, a class of medications called glycopeptides antibiotics, is derived from *Amycolatopsis orientalis*. It is the preferred treatment mechanism for patients suffering from serious MRSA infections, and is given orally or intravenously. Intravenous or oral administration of vancomycin is associated with a high degree of adverse reactions with the kidney and liver, and in some cases can result in lethal outcomes. These delivery mechanisms have not been useful for MRSA infections located on the skin or associated with wounds. Accordingly, a need exists for an effective MRSA composition which does not need to be given orally or intravenously.

DESCRIPTION OF THE PRIOR ART

Wound dressings designed to speed up healing are known in the art. For example, U.S. Pat. No. 6,201,164 describes a hydrocolloid composition wound gel having a water insoluble, water swellable cross-linked cellulose derivative and an alginate. U.S Patent Publication 2009/0317467 describes a wound gel having a particulate dispersion of one hydrocolloid in a low water activity anti-microbial matrix. U.S. Pat. Nos. 7,169,406 and 6,331,309 describe wound healing compositions which contain growth factors. While each of the cited art describes various wound healing compositions, none contemplate the use of an antibiotic which may be useful in killing or preventing the growth of MRSA.

Wound gels containing antibiotics are also known in the art. For example, U.S. Pat. No. 6,914,051 describes a compound and method for the treatment of microbial infection affecting the sub-dermal soft tissue. The compound contains a macrolide antibiotic and a PLO gel. U.S. Pat. No. 5,905,092 describes a composition having a topical semisolid composition which is described as providing a moist environment for a wound. The composition comprises polyhydric alcohols, gelling agents, and an antibiotic formulation. Neither of these cited references contemplates the use of an antibiotic for the treatment of MRSA. Song-Hu Lin et al., (1999) In Vitro Elution of Antibiotic-Impregnated Biodegradable Calcium Alginate Wound Dressing, J of Trauma: Injury, Infection and Critical Care, Vol. 47(1), 136-141, describe a calcium alginate wound dressing which contains vancomycin. The delivery system described therein, however, had limited stability and potency and suffered from the potential of resulting in foreign body reaction if left on the wound for too long of a time period.

SUMMARY OF THE INVENTION

The present invention describes a composition and method of using the composition for the treatment of MRSA in wounds. The composition is based on a gel composition containing one or more polymers, preservatives, and/or pH stabilizers and buffers having wound healing properties. Compounded into the gel formulation is at least one agent which is effective against resistant type microbes. The composition is characterized by the antibiotic agent having sustained potency and stability. By incorporating the drug into a gel composition that is formulated to enhance wound healing, the treatment of such disease is possible in a manner which promotes wound healing while reducing or eliminating the MRSA microbe. Preferably, the drug is one or more antibiotic agents in therapeutically effective concentrations to reduce or eliminate MRSA.

As used herein, the term "wound" is defined as an injury to any tissue, and includes burns, lacerations, abrasions, bites, surgical wounds, puncture wounds, ulcers, including but not limited to acute and chronic wounds from complicated skin and soft tissue infection (cSSTI), acute and chronic wounds from skin and skin structure infection (SSSI) venous stasis ulcers, diabetic ulcers, pressure ulcers, post surgical ulcers, post traumatic ulcers and spontaneous ulcers.

As used herein, the term "therapeutically effective concentrations" is defined as the concentration or amount of the antibiotic agent sufficient to result in or produce preventative, healing, curative, stabilizing, ameliorative effect in the treatment of the treatment site or condition, and may include reduction or elimination of MRSA.

Accordingly, it is an objective of the instant invention to provide a topical bactericidal gel for the inhibition of microbial growth in a wound, characterized by an antibiotic agent having sustained potency and stability.

It is a further objective of the instant invention to provide a topical gel composition for the treatment of resistant-type microbes in a wound characterized by an antibiotic agent which has sustained potency and stability.

It is a still further objective of the instant invention to provide a topical bactericidal gel containing an effective amount of vancomycin having sustained potency and stability.

It is yet another objective of the instant invention to provide a composition gel for the treatment of Methicillin-resistant *Staphylococcus aureus* (MRSA) characterized by having vancomycin which has sustained potency and stability.

It is a still further objective of the instant invention to provide a method of treating Methicillin-resistant *Staphylococcus aureus* (MRSA) by administering a composition characterized by having vancomycin which has sustained potency and stability.

It is a further objective of the instant invention to provide a composition gel for the treatment of Methicillin-resistant *Staphylococcus aureus* (MRSA) characterized by having vancomycin which has sustained potency for greater than 2 years.

It is yet another objective of the instant invention to provide a composition gel for the treatment of Methicillin-resistant *Staphylococcus aureus* (MRSA) characterized by having vancomycin which has sustained stability for greater than 2 years.

It is a still further objective of the invention to provide a method of treating Methicillin-resistant *Staphylococcus aureus* (MRSA) by administering to a treatment site a composition characterized by having vancomycin which has sustained potency for greater than 2 years.

It is a further objective of the instant invention to provide a method of treating Methicillin-resistant *Staphylococcus aureus* (MRSA) by administering to a treatment site a composition characterized by having vancomycin which has sustained potency for greater than 2 years.

It is yet another objective of the instant invention to provide a composition gel for the treatment of Methicillin-resistant *Staphylococcus aureus* (MRSA) characterized by having vancomycin which has sustained potency and stability and maintains a moist wound environment to enhance wound healing.

It is a still further objective of the invention to provide a homogenous gel for the treatment of Methicillin-resistant *Staphylococcus aureus* (MRSA) characterized by having vancomycin which has sustained potency and stability and maintains contact to the treatment site thereby increasing the efficiency of the action of the vancomycin.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
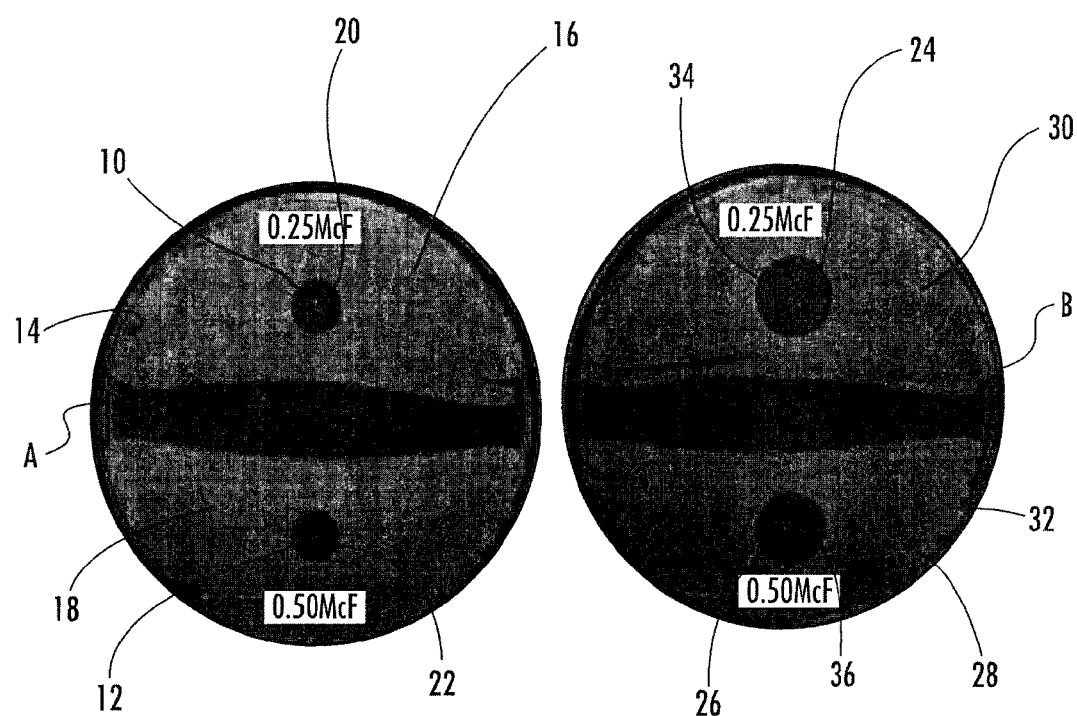
FIG. 1 illustrates the inhibition of microbial growth associated with the vancomycin gel compound in accordance with the instant invention, showing zones of inhibition for both vancomycin compositions which have been stored at room temperature or at refrigerated temperatures.
Figure 2:
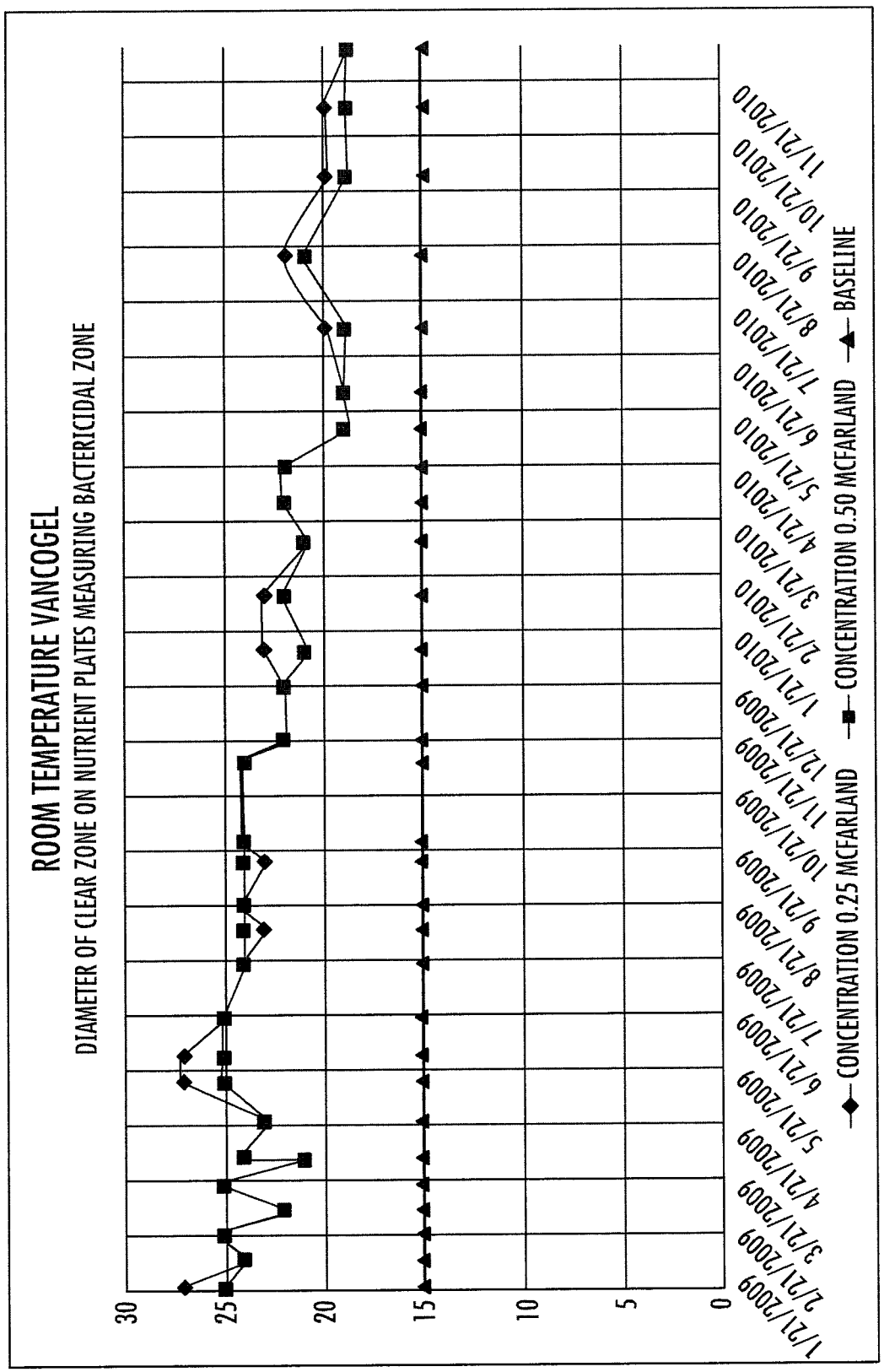
FIG. 2 is a graph showing the diameters of the zone of inhibition tests for the vancomycin gel stored at room temperature over a period of 23 months.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention is directed to an enhanced wound healing composition, including a gel composition in combination with an antibiotic agent, such as vancomycin, useful for the prevention of the spread of resistant-type bacteria and/or gram positive organisms. The composition, when placed in contact with a treatment site, such as a wound infection, delivers the antibiotic agent to the site. While the composition may be used in the topical treatment of sites infected by *Staphylococcus aureus* bacteria generally, the present invention is preferably directed to the treatment of Methicillin-resistant *Staphylococcus aureus* (MRSA). The unique aspect of the composition in accordance with the instant invention is in providing a composition which not only maintains a moist wound environment to enhance wound healing, but also provides a composition having an antibiotic agent which has sustained potency and stability. Sustained potency and stability over an extended time period is particularly useful in disease environments that may require extended treatment options and reduction in production of the gel. A sustained potent and stable vancomycin wound gel would also be beneficial for shipping as shipping a stable gel at room temperature reduces costs.

The preferred antibiotic agent in accordance with the instant invention is vancomycin, vancomycin HCL or salts of vancomycin. However, any antibiotic, such as but not limited to, deptomycin, doxycycline, linezolid, that is effective to reduce or eliminate MRSA and can be compounded into a topical formulation may be used. Vancomycin is a class of medications called glycopeptides antibiotics. It is a tricyclic glycopeptides antibiotic that is derived from *Amycolatopsis orientalis*. It has the molecular formula $C_{66}H_{75}C_{12}N_9O_{24}$—HCL. The bactericidal action of vancomycin primarily results from the inhibition of bacterial cell-wall biosynthesis. In addition, vancomycin acts to alter bacterial cell membrane permeability and RNA synthesis. Vancomycin has been FDA approved for many years, and is typically prescribed for the treatment of colitis or as a last means of fighting disease when other drugs have failed. While vancomycin is given either intravenously or orally, it was discovered that vancomycin could be incorporated into a gel composition in order to provide a composition which can be used for the treatment of MRSA in wounds. By formulating the compound in accordance with the instant invention, the inventor discovered that vancomycin had enhanced stability and potency over an extended period of time not previously known in the art.

Preferably, the antibiotic agent is compounded with a gel composition that has several characteristics which make it effective for wound healing. Accordingly, the gel composition must contain components that 1) accelerate wound healing, 2) are non-toxic, 3) do not produce any local tissue reaction; 4) have minimal expected allergic reactions, 5) maintain a moist wound environment, 6) maintain contact to wound areas thereby increasing the efficiency of action of the delivered drug, and 7) provide an environment that results in prolonged stability and potency for the antibiotic agent.

The composition is based on a gel composition containing one or more polymers, preservatives, and/or pH stabilizers and buffers in combination with an effective amount of an antibiotic to treat MRSA. The gel composition may be based on a combination of one or more of, 1) polyhydric alcohols, 2) polymeric gelling agents, such as but not limited to, hydroxyethycicellulose, hyrdoxypropylcellulose, carboxymethylcellulose (CMC), hydroxymethyl-cellulose, methyl-celulose, polyvinylppyrrolidine, 3) cross-linked acrylic acid polymers, such as CARBOPOL, CARBOPOL 940, CARBOPOL Utrez 10, CARBOPOL Ultrez 21, carrageenan, agar, gelatin, PVM/MA decadiene, cross polymer and ammonium acrylates/acrylonitrogen, 4) self gelling sodium or calcium alginate, such as but not limited to KELSTAT, having 6-7% sodium minerals and about 2.5-3% calcium minerals, or algenic acid sodium salt, 5) pH buffers or agents that resist changes in pH, such as but not limited to triethanolamine 6) microbial and/or fungal preservatives, such as dimethylol dimethylhydantoin (DMDM hydantoin), boric acid, potassium sorbate, ammonia compounds, paraben, 7) organic compounds, such as propylene glycol or glycerin which may act as oil dispersants or solvents, and 8) emulsifiers or surfactants, such as triethanolamine.

Example 1

| Ingredient | weight |
| --- | --- |
| DI Water | QS |
| Gel forming compounds | up to 10.0 |
| Preservative and buffering agents | up to 5.0 |

MRSA effective antibiotic: therapeutically effective amount

Example 2

| Ingredient | weight | weight(grams) |
| --- | --- | --- |
| DI Water | Q.S. | |
| Potassium Sorbate | 0.0-0.2 | 0.0-2.0 |
| DMDM Hydantoin | 0.0-0.1 | 0.0-1.0 |
| Boric Acid | 0.0-0.5 | 0.0-5.0 |
| CMC | 0.0-1.0 | 0.0-1.0 |
| Sodium/Calcium Alginate | 0.0-2.0 | 0.0-2.0 |
| Carbopol 940 | 0.0-0.5 | 0.0-5.0 |
| Propylene glycol | 0.0-10.0 | 0.0-100.0 |
| Triethanolamine | 0.0-0.5 | 0.0-5.0 |

MRSA reducing antibiotic: therapeutically effective amount

Example 3

| Ingredient | weight % | weight (grams) |
| --- | --- | --- |
| DI Water | 87.0 | 870.0 |
| Potassium Sorbate | 0.2 | 2.0 |
| DMDM Hydantoin | 0.1 | 1.0 |
| Boric Acid | 0.5 | 5.0 |
| CMC | 0.1 | 1.0 |
| Sodium/Calcium Alginate | 0.5 | 5.0 |
| Carbopol 940 | 0.5 | 5.0 |
| Propylene glycol | 10.0 | 100.0 |
| Triethanolamine | 0.5 | 5.0 |
| Vancomycin | 2.0 | 20.0 |

Preparation of Vancomycin Wound Gel: The vancomycin wound gel was prepared using sterile techniques within a sterile environment. Quality assurance techniques were employed to ensure a high quality compound. To ensure sterility and avoidance of contamination, a horizontal and vertical laminar hood was used to maximize sterility. Purified Vancomycin HCL, sterile, USP, off white lyophilized powder was obtained from a commercial source (Hospira, Inc., Lake Forest, Ill., USA). To a sterile vial containing 1 gram of the purified Vancomycin, sterile de-ionized water was added to obtain a concentration of 50 mg/ml. The reconstituted vancomycin was filtered using a 5 micron filter needle in order to remove any particulate matter that was present. To the other components that formulate the wound gel, namely the Potassium Sorbate, DMDM Hydantoin, Boric Acid, Sodium/Calcium Alginate, Carbopol 940, Propylene glycol, and Triethanolamine, reconstituted vancomycin was added to form the vancomycin wound gel composition. Preferably, the non-antibiotic agent components are mixed together prior to compounding with the reconstituted vancomycin to form a wound gel in a manner as described by U.S. Pat. No. 5,670,169. Alternatively, the commercial embodiment of the gel can be purchased under the trademark name of SAFGEL (Convatac, Skillman, N.J., USA). The gel and the vancomycin are then compounded together in aliquots of 20 ml. Each aliquot is stirred with a sterile glass rod in a sterile 60 ml syringe to an acceptable homogenous state. The homogenous gel was transferred to 10 ml syringes. Each of the 20 ml aliquots was formulated by instilling 400 mg of vancomycin into a syringe. This was followed by adding the gel until the final 20 ml aliquot was achieved. Syringes were filled to a volume expressed in milliliters with the final concentration at 20 mg/ml. The syringes were capped with sterile Luer-locks and stored for future use.

The final compounded product was then inspected for various characteristics, including uniformity of appearance, particulate matter, or other visual incompatibilities. After several days past compounding, no synersis (instability in aqueous and non-aqueous gels), discoloration, or particulate mater was found. Additionally, sterility testing was performed to ensure the final product was free of any bacteria or fungi.

Kirby Bauer Zone of Inhibition test—enhanced potency and stability testing procedures:

The vancomycin gel illustrated in Example 3 was tested for stability and potency. In compounding the vancomycin with the wound gel to form the vancomycin wound gel, the inventors found an unexpected result. The gel not only could be used to treat MRSA infections topically, but the vancomycin maintained its potency and stability for over 2 years. The enhanced potency and stability was in contrast to previous prior art which described a dressing with vancomycin having stability of less than 30 days, see Song-Shu Lin et al., (1999)

In vitro Elution of Antibiotic from Antibiotic-Impregnated Biodegradable Calcium Alginate Wound Dressing, *J Trauma*, Vol. 47(1), 136-141.

Vancomycin Gel Maintained at Room Temperature: A sterile saline solution aliquot in a clear tube was inoculated with a colony of Methicillin-resistant *Staphylococcus aureus* at 0.25 McFarland turbidity (as determined by using a densimeter). Another sterile saline solution was inoculated with a colony of Methicillin-resistant *Staphylococcus aureus* at 0.50 McFarland turbidity (as determined by using a densimeter). A dividing line was drawn through a Mueller Hinton Agar plate. A cotton swab was used to inoculate the top half of the plate with the 0.25 McFarland Methicillin-resistant *Staphylococcus aureus* to obtain a thin lawn of the organism. A second cotton swab was used to inoculate the lower half of the plate with the 0.50 McFarland Methicillin-resistant *Staphylococcus aureus* to obtain a thin lawn of the organism. On each half of the plate, approximately two microliters of the vancomycin gel, which when not in use was stored at room temperature, i.e. maintained at around 20-25 degrees Celsius, was placed in the center of the lawn of the Methicillin-resistant *Staphylococcus aureus*. The plates were allowed to incubate in an air incubator maintained at 35 degrees Celsius for 18-24 hours. After the 18-24 hour incubation period, a measurement of the effectiveness was undertaken by measuring the area of no growth around the vancomycin gel using techniques known in the art.

Referring to FIG. 1, illustrative results of the Kirby-Bauer zone of inhibition test is shown. Plate A illustrates two disks of the vancomycin compound 10 and 12, which has been stored at room temperature, placed in a lawn of a Methicillin-resistant *Staphylococcus aureus* 14 as described above. The top portion 16 represents the microbes plated at 0.25 McFarland turbidity and the bottom portion 18 represents the microbes plated at 0.50 McFarland turbidity. Zones of inhibition 20 and 22 are evident around the disks 10 and 12, indicating the ability of the vancomycin gel to inhibit the growth of the MRSA over the 18-24 hour period of contact. The zones of inhibition appearing around the vancomycin gel disks indicate substantial antimicrobial activity as the zone of inhibition on the agar plate remains free from microbial growth. The plate testing was carried out for an extended time period, a period in excess of 2 years, in order to characterize the potency and stability of the vancomycin gel. Table 1 shows the individual time periods and corresponding zone of inhibition measurements, in millimeters (mm), for the vancomycin gel stored at room temperature for plates plated with 0.25 and 0.5 McFarland Methicillin-resistant *Staphylococcus aureus*. As shown in FIG. 1, the diameter of the clear zone at both concentrations was well above the standard 15 mm baseline and remained that way for a period of about 2 years. Referring back to Table 1, the data indicates that the zone of inhibition measurements did not drop below the standard 15 mm for a time period of at least 2 years and 3 months.

TABLE 1

| | Zone of Inhibition Results of Vancomycin Composition at Room Temperature: | |
|---|---|---|
| Date of Test | Zone of Inhibition (mm): Concentration 0.25 McFarland | Zone of Inhibition (mm): Concentration 0.50 McFarland |
| Jan. 21, 2009 | 27 | 25 |
| Feb. 5, 2009 | 24 | 24 |
| Feb. 19, 2009 | 25 | 25 |
| Mar. 4, 2009 | 22 | 22 |
| Mar. 18, 2009 | 25 | 25 |
| Apr. 1, 2009 | 21 | 21 |
| Apr. 2, 2009 | 24 | 24 |
| Apr. 22, 2009 | 23 | 23 |
| May 13, 2009 | 27 | 25 |
| May 27, 2009 | 27 | 25 |
| Jun. 17, 2009 | 25 | 25 |
| Jul. 17, 2009 | 24 | 24 |
| Aug. 5, 2009 | 23 | 24 |
| Aug. 19, 2009 | 24 | 24 |
| Sep. 12, 2009 | 23 | 24 |
| Sep. 23, 2009 | 24 | 24 |
| Nov. 6, 2009 | 24 | 24 |
| Nov. 19, 2009 | 22 | 22 |
| Dec. 19, 2009 | 22 | 22 |
| Jan. 8, 2010 | 21 | 21 |
| Feb. 8, 2010 | 22 | 22 |
| Mar. 10, 2010 | 21 | 21 |
| Apr. 1, 2010 | 22 | 22 |
| Apr. 21, 2010 | 22 | 22 |
| May 12, 2010 | 19 | 19 |
| Jun. 1, 2010 | 19 | 19 |
| Jul. 7, 2010 | 20 | 19 |
| Aug. 16, 2010 | 22 | 21 |
| Sep. 29, 2010 | 20 | 19 |
| Nov. 6, 2010 | 20 | 19 |
| Dec. 8, 2010 | 19 | 19 |
| Jan. 21, 2011 | 19 | 19 |
| Apr. 27, 2011 | 17 | 16 |
| Oct. 4, 2011 | 13 | 13 |

Vancomycin Wound Gel Maintained Refrigerated Temperatures of about 3-5 Degrees Celsius: A sterile saline solution aliquot in a clear tube was inoculated with a colony of Methicillin-resistant *Staphylococcus aureus* of 0.25 McFarland turbidity (as determined by using a densimeter). Another sterile saline solution was inoculated with a colony of Methicillin-resistant *Staphylococcus aureus* of 0.50 McFarland turbidity (as determined by using a densimeter). A dividing line was drawn through a Mueller Hinton Agar plate. A cotton swab was used to inoculate the top half of the plate with the 0.25 McFarland Methicillin-resistant *Staphylococcus aureus* to obtain a thin lawn of the organism. A second cotton swab was used to inoculate the lower half of the plate with the 0.50 McFarland Methicillin-resistant *Staphylococcus aureus* to obtain a thin lawn of the organism. On each half of the plate, approximately two microliters of the vancomycin wound gel stored in a refrigerator maintained at around 3-5 degrees Celsius was placed in the center of the lawn of the Methicillin-resistant *Staphylococcus aureus*. The plates were allowed to incubate in an air incubator which was maintained at 35 degrees Celsius for 18-24 hours. After the 18-24 hour incubation period, a measurement of the effectiveness was undertaken by measuring the area of no growth around the vancomycin gel using techniques known in the art.

Referring back to FIG. 1, illustrative results of the Kirby-Bauer zone of inhibition test is shown. Plate B illustrates two disks of the vancomycin compound 24 and 26, which has been stored at temperatures of between 3-5 degrees Celsius and placed in a lawn of a Methicillin-resistant *Staphylococcus aureus* 28 as described above. The top portion 30 represents the microbes plated at 0.25 McFarland turbidity and the bottom portion 32 represents the microbes plated at 0.50 McFarland turbidity. Zones of inhibition 34 and 36 are evident around the disks 24 and 26, indicating the ability of the vancomycin gel to inhibit the growth of the MRSA over the 18-24 hour period of contact. The zones of inhibition appearing around the vancomycin gel disks indicate substantial antimicrobial activity as the zone of inhibition on the agar plate remains free from microbial growth. The plate testing was carried out for an extended time period, a period in excess of 2 years, in order to characterize the potency and stability of the vancomycin gel.

Figure 3:
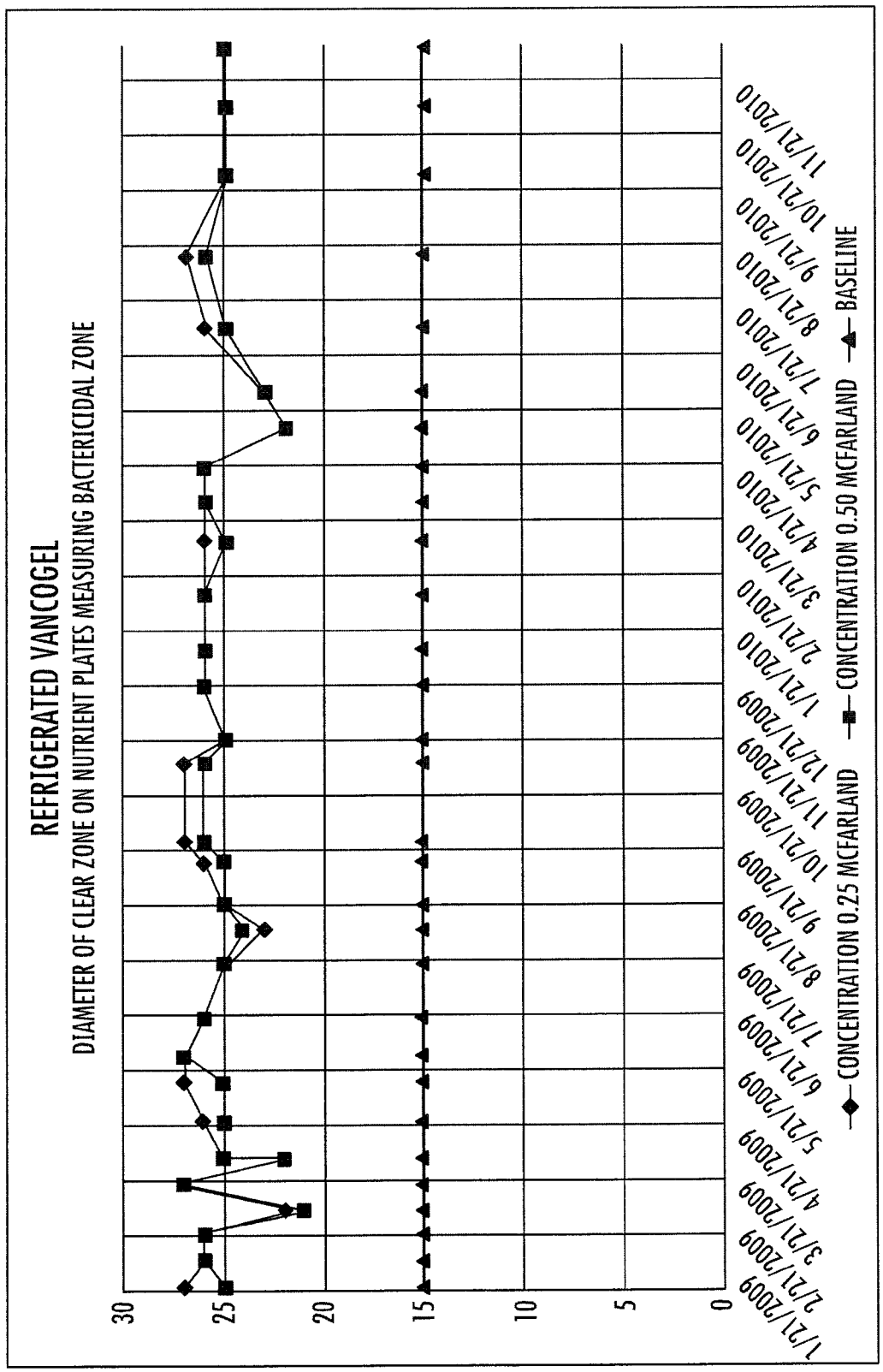
FIG. 3 is a graph showing the diameters of the zone of inhibition tests for the vancomycin gel stored at refrigerated temperatures over a period of 23 months.

Table 2 shows the individual time periods and corresponding zone of inhibition measurements, in millimeters (mm), for the vancomycin gel stored at 0-3 degrees Celsius for plates plated with 0.25 and 0.5 McFarland Methicillin-resistant *Staphylococcus aureus*. As shown in FIG. 3, the diameter of the clear zone at both concentrations was well above the standard 15 mm baseline and remained that way for a period over nearly 2 years. Referring back to Table 2, the data indicates that the zone of inhibition measurements did not drop below the standard 15 mm for a time period of at least 2 years and 3 months. Unlike the vancomycin gel stored at room temperature, the zone of inhibition for the vancomycin stored at 3-5 degrees Celsius had a value that remained over 20 mm, and did not see a decline in value below the 15 mm standard during the time period tested.

TABLE 2

Results of Zone of Inhibition Testing for
Vancomycin Gel Stored at 3-5 Degrees:

| Date of Test | Zone of Inhibition: Concentration 0.25 McFarland | Zone of Inhibition: Concentration 0.50 McFarland |
| --- | --- | --- |
| Jan. 21, 2009 | 27 | 25 |
| Feb. 5, 2009 | 26 | 26 |
| Feb. 19, 2009 | 26 | 26 |
| Mar. 4, 2009 | 22 | 21 |
| Mar. 18, 2009 | 27 | 27 |
| Apr. 1, 2009 | 22 | 22 |
| Apr. 2, 2009 | 25 | 25 |
| Apr. 22, 2009 | 26 | 25 |
| May 13, 2009 | 27 | 25 |
| May 27, 2009 | 27 | 27 |
| Jun. 17, 2009 | 26 | 26 |
| Jul. 17, 2009 | 25 | 25 |
| Aug. 5, 2009 | 23 | 24 |
| Aug. 19, 2009 | 25 | 25 |
| Sep. 12, 2009 | 26 | 25 |
| Sep. 23, 2009 | 27 | 26 |
| Nov. 6, 2009 | 27 | 26 |
| Nov. 19, 2009 | 25 | 26 |
| Dec. 19, 2009 | 26 | 25 |
| Jan. 8, 2010 | 26 | 26 |
| Feb. 8, 2010 | 26 | 26 |
| Mar. 10, 2010 | 26 | 25 |
| Apr. 1, 2010 | 26 | 26 |
| Apr. 21, 2010 | 26 | 26 |
| May 12, 2010 | 22 | 22 |
| Jun. 1, 2010 | 23 | 23 |
| Jul. 7, 2010 | 26 | 25 |
| Aug. 16, 2010 | 27 | 26 |
| Sep. 29, 2010 | 25 | 25 |
| Nov. 6, 2010 | 25 | 25 |
| Dec. 8, 2010 | 25 | 25 |
| Jan. 21, 2011 | 27 | 27 |
| Apr. 27, 2011 | 26 | 22 |
| Oct. 4, 2011 | 21 | 21 |

Anticipated method of treatment: Based on the results of the zone of inhibition tests, it is anticipated that the vancomycin wound gel in accordance with the instant invention can be used for the treatment of a treatment site having or being suspected of having Methicillin-resistant *Staphylococcus aureus* (MRSA). Patients having or suspected of having MRSA in a wound are identified. A determination as to whether or not the patient actually has MRSA may be accomplished by physical examination, identification of the type of ulcer, tissue biopsy, or culturing the site and positively identifying MRSA as known to one of skill in the art. Once the site has been determined or suspected of being MRSA positive, the user applies the composition in accordance with the instant invention, namely the gel composition characterized by an antibiotic agent which has sustained potency and stability comprising, in combination a wound gel having potassium sorbate at a concentration of about 0.2% wt/wt; DMDM hydantoin at a concentration of about 0.1% wt/wt; Boric acid at a concentration of about 0.5% wt/wt; CMC at a concentration of about 0.1% wt/wt; Sodium/calcium alginate mixture at a concentration of about 0.5% wt/wt; a cross-linked polyacrylate polymer at a concentration of about 0.5% wt/wt; propylene glycol at a concentration of about 10.0% wt/wt; triethanolamine at a concentration of about 0.5% wt/wt; a sufficient quantity of deionized water to form the composition, and an antibiotic, such as but not limited to vancomycin, at a therapeutically effective concentration to reduce the amount of microbial organisms which result in MRSA infection, to a treatment site having or being suspected of having MRSA. The application of the vancomycin compound can be placed at any site along the entire body. The composition is preferably placed onto the wound using sterile techniques, such as through the use of a sterile syringe. The vancomycin gel compound is expressed onto the treatment site, preferably covering the entire site with the gel. Additional vancomycin wound gel can be applied as needed. The application of the composition to the treatment site results in reduction, or elimination of MRSA at the treatment site. Once the MRSA has been eliminated or reduced, the treatment site can further recover.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A topical bactericidal composition for the inhibition of microbial growth in a wound, characterized by an antibiotic agent which has sustained potency and stability comprising, in combination:
   a wound healing composition comprising one or more polymers, one or more preservatives, one or more pH stabilizers and one or more buffers, which in combination, maintain sustained potency or stability of at least one antibiotic agent for at least a time period of between 1 month and 22 months; and
   at least one antibiotic agent in an effective amount for killing or preventing microbial growth of Methicillin-resistant *Staphylococcus aureus* (MRSA) within a wound site.

2. The topical bactericidal composition in which the bactericidal agent has sustained potency and stability according to claim 1 wherein said wound healing composition comprises sodium/calcium alginate, a cross-linked polyacrylate polymer, propylene glycol, triethanolamine, or combinations thereof.

3. The topical bactericidal composition in which the bactericidal agent has sustained potency and stability according to claim 1 wherein said antibiotic agent is a glycopeptide antibiotic.

4. The topical bactericidal composition in which the bactericidal agent has sustained potency and stability according to claim 1 wherein said antibiotic agent is vancomycin or vancomycin HCl.

5. The topical bactericidal composition in which the bactericidal agent has sustained potency and stability according to claim 1 wherein said vancomycin or vancomycin HCl has a concentration of 1.25 to 1.5%.

6. A composition for the treatment of Methicillin-resistant *Staphylococcus aureus* (MRSA) characterized by an antibiotic agent having sustained potency and stability comprising, in combination with the following components:
   potassium sorbate at a concentration ranging from 0.01 to 0.2% wt/wt;
   DMDM hydantoin at a concentration ranging from 0.01 to 0.1% wt/wt;
   Boric acid at a concentration ranging from 0.01 to 0.5% wt/wt;
   CMC at a concentration ranging from 0.01 to 0.1% wt/wt;
   Sodium/calcium alginate mixture at a concentration ranging from 0.01 to 0.5% wt/wt;
   a cross-linked polyacrylate polymer at a concentration ranging from 0.01 to 0.5% wt/wt;
   propylene glycol at a concentration ranging from 0.01 to 10.0% wt/wt;
   triethanolamine at a concentration ranging from 0.01 to 0.5% wt/wt;
   a sufficient quantity of deionized water; and
   an antibiotic agent at an effective concentration to reduce the amount of microbial organisms which result in MRSA infection, said antibiotic agent, in combination with said components, maintains a stability and potency for at least a time period of between 1 month and 22 months.

7. The composition for the treatment of Methicillin-resistant *Staphylococcus aureus* (MRSA) characterized by an antibiotic agent having sustained potency and stability according to claim 6 wherein said antibiotic is vancomycin or vancomycin HCl.

8. The composition for the treatment of Methicillin-resistant *Staphylococcus aureus* (MRSA) characterized by an antibiotic agent having sustained potency and stability according to claim 7 wherein said vancomycin or vancomycin HCl is at a concentration of about ranging from 0.01 to 2% wt/wt.

9. The composition for the treatment of Methicillin-resistant *Staphylococcus aureus* (MRSA) characterized by an antibiotic agent having sustained potency and stability according to claim 7 wherein said vancomycin or vancomycin HCl has a dosage of between 1.25% and 1.5%.

10. The composition for the treatment of Methicillin-resistant *Staphylococcus aureus* (MRSA) characterized by an antibiotic agent having sustained potency and stability according to claim 8 wherein said composition has a pH in the range of between about 4.5 and 7.0.

11. The composition for the treatment of Methicillin-resistant *Staphylococcus aureus* (MRSA) characterized by an antibiotic agent which has sustained potency and stability according to claim 8 wherein said composition, when stored at room temperature, maintains a zone of inhibition of greater than 15 mm for a period of at least 2 years when stored at room temperature.

12. The composition for the treatment of Methicillin-resistant *Staphylococcus aureus* (MRSA) characterized by an antibiotic agent which has sustained potency and stability according to claim 7 wherein said composition, when maintained at refrigerated temperatures, maintains a zone of inhibition greater than 20 mm for a period greater than 2 years.

13. A method for the treatment of Methicillin-resistant *Staphylococcus aureus* (MRSA) comprising: applying a composition characterized by an antibiotic agent which has sustained potency and stability comprising, in combination with the components of, potassium sorbate at a concentration ranging from 0.01 to 0.2% wt/wt; DMDM hydantoin at a concentration ranging from 0.01 to 0.1% wt/wt; Boric acid at a concentration ranging from 0.01 to 0.5 wt/wt; CMC at a concentration ranging from 0.01 to 0.1% wt/wt; Sodium/calcium alginate mixture at a concentration ranging from 0.01 to 0.5% wt/wt; a cross-linked polyacrylate polymer at a concentration ranging from 0.01 to 0.5% wt/wt; propylene glycol at a concentration ranging from 0.01 to 10.0% wt/wt; triethanolamine at a concentration ranging from 0.01 to 0.5% wt/wt; a sufficient quantity of deionized water to form the composition; and an antibiotic agent at an effective concentration to reduce the amount of microbial organisms which result in MRSA infection, said antibiotic agent in combination with said components maintains a stability and potency for at least a time period of between 1 month and 22 months, to a treatment site having or being suspected of having MRSA;
   wherein application of said composition to said treatment site results in reduction of said MRSA.

14. The method for the treatment of Methicillin-resistant *Staphylococcus aureus* (MRSA) according to claim 13 wherein said antibiotic is vancomycin or vancomycin HCl.

15. The method for the treatment of Methicillin-resistant *Staphylococcus aureus* (MRSA) according to claim 13 wherein said vancomycin or vancomycin HCl is at a concentration ranging from 0.01 to 2% wt/wt.

16. The method for the treatment of Methicillin-resistant *Staphylococcus aureus* (MRSA) according to claim 14 wherein said composition has a pH in the range of between about 4.5 and 7.0.

17. The method for the treatment of Methicillin-resistant *Staphylococcus aureus* (MRSA) according to claim 15 wherein said composition maintains a zone of inhibition of greater than 15 mm for a period of at least 2 years when stored at room temperature.

18. The method for the treatment of Methicillin-resistant *Staphylococcus aureus* (MRSA) according to claim 15 wherein said composition maintains a zone of inhibition of greater than 20 mm for a period greater than 2 years when stored at refrigerated temperatures.

19. The method for the treatment of Methicillin-resistant *Staphylococcus aureus* (MRSA) according to claim 13 further including the step of identifying MRSA infection at said treatment site prior to applying said composition.

20. The method for the treatment of Methicillin-resistant *Staphylococcus aureus* (MRSA) according to claim 13 wherein said treatment site is a skin wound.

21. The method for the treatment of Methicillin-resistant *Staphylococcus aureus* (MRSA) according to claim 20 wherein said treatment site is a venous stasis ulcer, diabetic ulcer, pressure ulcer, post-surgical ulcer, post traumatic ulcer, spontaneous ulcer, or combinations thereof.

22. The method for the treatment of Methicillin-resistant *Staphylococcus aureus* (MRSA) according to claim 20 wherein said treatment site is an acute wound in complicated skin and soft tissue infection (cSSTI) or complicated skin and skin structure infections (cSSSI).

23. The method for the treatment of Methicillin-resistant *Staphylococcus aureus* (MRSA) according to claim 20 wherein said treatment site is a chronic wound in complicated skin and soft tissue infection (cSSTI) or complicated skin and skin structure infections (cSSSI).

24. The composition for the treatment of Methicillin-resistant *Staphylococcus aureus* (MRSA) characterized by an antibiotic agent having sustained potency and stability according to claim 6 wherein said antibiotic agent in combination with said components maintains a stability and potency for a time period of between 1 month and 12 months.

25. The composition for the treatment of Methicillin-resistant *Staphylococcus aureus* (MRSA) characterized by an antibiotic agent having sustained potency and stability according to claim 6 wherein said antibiotic agent in combination with said components maintains a stability and potency for a time period of between 1 month and 3 months.

26. The method for the treatment of Methicillin-resistant *Staphylococcus aureus* (MRSA) according to claim 13 wherein said antibiotic agent in combination with said components maintains a stability and potency for a time period of between 1 month and 12 months.

27. The method for the treatment of Methicillin-resistant *Staphylococcus aureus* (MRSA) according to claim 13 wherein said antibiotic agent in combination with said components maintains a stability and potency for a time period of between 1 month and 3 months.

28. A topical bactericidal composition for the inhibition of microbial growth in a wound, characterized by an antibiotic agent which has sustained potency and stability comprising, in combination:
   a wound healing gel composition, said gel comprising one or more gel forming agents, one or more polymers, one or more preservatives, one or more pH stabilizers and one or more buffers, which in combination, maintain antibiotic agent potency and stability, each component of said composition in a sufficient concentration to maintain sustained potency or stability of at least one antibiotic agent for at least a time period of between 1 month and 22 months; and
   at least one antibiotic agent in an effective amount for killing or preventing microbial growth of Methicillin-resistant *Staphylococcus aureus* (MRSA) within a wound site.

* * * * *